(12) United States Patent
McDevitt et al.

(10) Patent No.: US 10,758,451 B1
(45) Date of Patent: Sep. 1, 2020

(54) HAND STIMULATION DEVICE TO FACILITATE THE INVOCATION OF A MEDITATIVE STATE

(71) Applicant: Core Wellness, Inc., Piedmont, CA (US)

(72) Inventors: Sarah McDevitt, Oakland, CA (US); Brian Bolze, San Francisco, CA (US)

(73) Assignee: CORE WELLNESS, INC., Piedmont, CA (US)

( * ) Notice: Subject to any disclaimer, the term of this patent is extended or adjusted under 35 U.S.C. 154(b) by 555 days.

(21) Appl. No.: 15/590,885

(22) Filed: May 9, 2017

Related U.S. Application Data

(60) Provisional application No. 62/333,699, filed on May 9, 2016.

(51) Int. Cl.
*A61H 23/00* (2006.01)
*A61B 5/04* (2006.01)
*A61B 5/0452* (2006.01)

(52) U.S. Cl.
CPC ......... *A61H 23/00* (2013.01); *A61B 5/04012* (2013.01); *A61B 5/0452* (2013.01); *A61H 2201/5043* (2013.01); *A61H 2201/5097* (2013.01); *A61H 2205/065* (2013.01); *A61H 2230/04* (2013.01)

(58) Field of Classification Search
CPC .... A61H 23/00; A61H 23/02; A61H 23/0218; A61H 23/0236; A61H 23/0245; A61H 23/0254; A61H 23/0263; A61H 23/04; A61H 2201/50; A61H 2201/5002; A61H 2201/5007; A61H 2201/0173; A61H 2201/0176; A61H 2201/018; A61H 2205/065; A61H 2230/04; A61H 2201/5005–5015; A61H 2201/0138–0149; A61H 19/00–50; A61M 2021/0022
USPC .............................................. 601/46, 48, 84
See application file for complete search history.

(56) References Cited

U.S. PATENT DOCUMENTS

| | | | | |
|---|---|---|---|---|
| 5,297,981 A * | 3/1994 | Maxim | ................ | A63H 33/005 446/437 |
| 5,575,761 A * | 11/1996 | Hajianpour | ........ | A61H 23/0263 601/48 |
| 2007/0179414 A1 * | 8/2007 | Imboden | ................ | A61H 19/00 601/72 |
| 2013/0253388 A1 * | 9/2013 | Juto | ..................... | A61H 9/0078 601/48 |
| 2015/0119770 A1 * | 4/2015 | Driscoll | ................ | A61H 23/02 601/48 |

(Continued)

*Primary Examiner* — Samchuan C Yao
*Assistant Examiner* — Matthew Standard
(74) *Attorney, Agent, or Firm* — Cooley LLP

(57) ABSTRACT

An apparatus has a bottom sphere and a top sphere connected to the bottom sphere to define an interior volume with a central plane. The top sphere includes a concave surface at an angle to the central plane. A motor is positioned within the interior volume. A processor is positioned within the interior volume and is connected to the motor. A memory is positioned within the interior volume and is connected to the processor. The memory stores instructions executed by the processor. The instructions include hand stimulation sessions. Each hand stimulation session comprises a sequence of cycles, where each cycle is a sequence of vibration intensity values applied to the motor.

20 Claims, 11 Drawing Sheets

(56) References Cited

U.S. PATENT DOCUMENTS

| | | | |
|---|---|---|---|
| 2015/0328082 A1* | 11/2015 | Jiang | A61H 19/00 600/38 |
| 2015/0351999 A1* | 12/2015 | Brouse | A61H 23/0263 601/74 |
| 2016/0074278 A1* | 3/2016 | Muench | A61H 23/02 601/46 |
| 2016/0199249 A1* | 7/2016 | Dunham | A61H 19/44 601/15 |
| 2017/0106249 A1* | 4/2017 | Marton | A63B 43/004 |
| 2017/0367923 A1* | 12/2017 | Bergbacka | A01K 13/002 |
| 2018/0185237 A1* | 7/2018 | Baetica | G08C 17/02 |
| 2019/0261313 A1* | 8/2019 | Borras | A61H 23/0218 |

* cited by examiner

1

HAND STIMULATION DEVICE TO FACILITATE THE INVOCATION OF A MEDITATIVE STATE

CROSS-REFERENCE TO RELATED APPLICATION

This application claims priority to U.S. Provisional Patent Application Ser. No. 62/333,699, filed May 9, 2016, the contents of which are incorporated herein by reference.

FIELD OF THE INVENTION

This invention relates generally to a hardware appliance operative with a mobile device executing an application. More particularly, the hardware appliance is in the form of a hand stimulation device to facilitate invocation of a meditative state.

BACKGROUND OF THE INVENTION

The salutary effects of meditation have been known for centuries. It would be desirable to leverage advances in technology to facilitate the invocation of a meditative state. More particularly, it would be desirable to provide a hardware appliance in the form of a hand stimulation device operative with a mobile device executing an application to facilitate the invocation of a meditative state.

SUMMARY OF THE INVENTION

An apparatus has a bottom sphere and a top sphere connected to the bottom sphere to define an interior volume with a central plane. The top sphere includes a concave surface at an angle to the central plane. A motor is positioned within the interior. A processor is positioned within the interior volume and is connected to the motor. A memory is positioned within the interior volume and is connected to the processor. The memory stores instructions executed by the processor. The instructions include hand stimulation sessions. Each hand stimulation session comprises a sequence of cycles, where each cycle is a sequence of vibration intensity values applied to the motor.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

Figure 1:
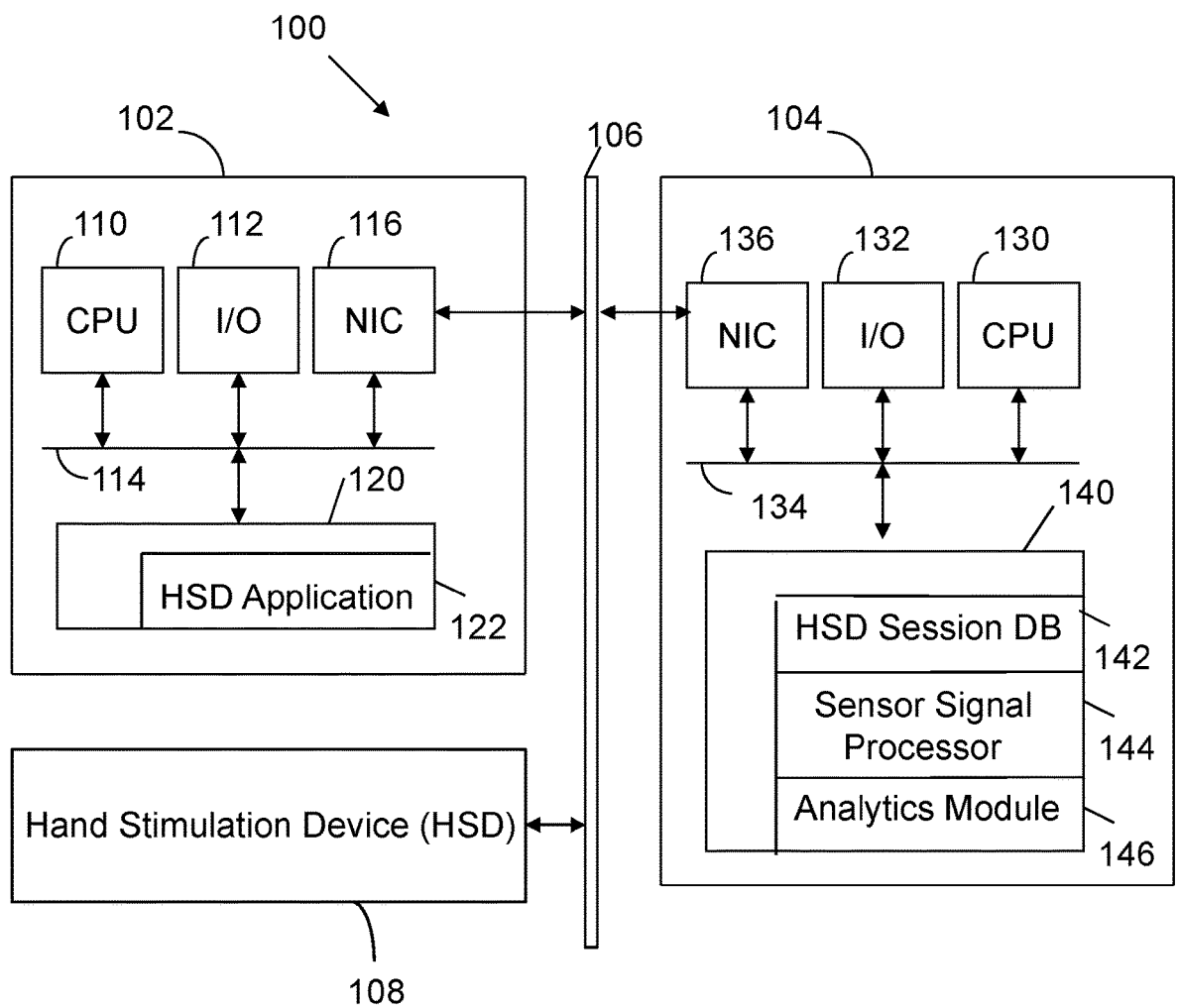
FIG. 1 illustrates a system configured in accordance with an embodiment of the invention.

FIG. 1 illustrates a system 100 configured in accordance with an embodiment of the invention. The system includes a client device 102 connected to a server 104 via a network 106, which may be any combination of wired and/or wireless networks. A hand stimulation device (HSD) 108 is also connected to the network 106.

The client device 106 may be a computer, a table, a mobile device, a wearable device and the like. The client device 106 includes a central processing unit 110 and input/output devices 112 connected via a bus 114. The input/output devices 112 may include a keyboard, mouse, touch display and the like. A network interface circuit 116 is also connected to the bus 114 to provide connectivity to network 106. A memory 120 is also connected to the bus 114. The memory 120 stores a hand stimulation device (HSD) application 122 with instructions executed by the central processing unit 110. The HSD application 122 is operative to interact with the HSD 108 via network 106, such as through a WiFi or Bluetooth® connection. The HSD application 122 is also operative to communicate with server 104.

Server 104 includes a central processing unit 130, input/output devices 132, a bus 134 and a network interface circuit 136. A memory 140 is connected to bus 134. The memory stores instructions executed by the central processing unit 130. In one embodiment, the memory 140 stores an HSD session database 142. The HSD session database 142 is a repository of hand stimulation sessions, where each hand stimulation session includes a sequence of cycles, where each cycle is a sequence of vibration intensity values applied to motor of the HSD 108. As a result, the HSD 108 vibrates. As demonstrated below, a user holds the HSD 108. The vibration intensity values are configured to invoke in the user a meditative state. Individual sessions of the HSD session database 142 are downloaded to client 102 and/or HSD 108 via network 106. The memory 140 also stores a sensor signal processor 144. The sensor signal processor 144 collects sensor signals from the hand stimulation device 108. The sensor signal processor 144 evaluates the signals and selectively provides feedback to the HSD application 122 for consumption by a user of the HSD 108. The memory 140 also stores an analytics module 146. The analytics module 146 includes instructions executed by the central processing unit 130 to supply HSD analytic information, such as HSD session participation history, sensor signal analytics, recommended HSD sessions and the like. In one embodiment, the HSD analytic information is conveyed over network 106 to the HSD application 122. An output device 112 (e.g., a display) of the client device 102 displays the HSD analytic information to a user. The HSD application 122 may also incorporate analytics that are generated and displayed locally.

Figure 2:
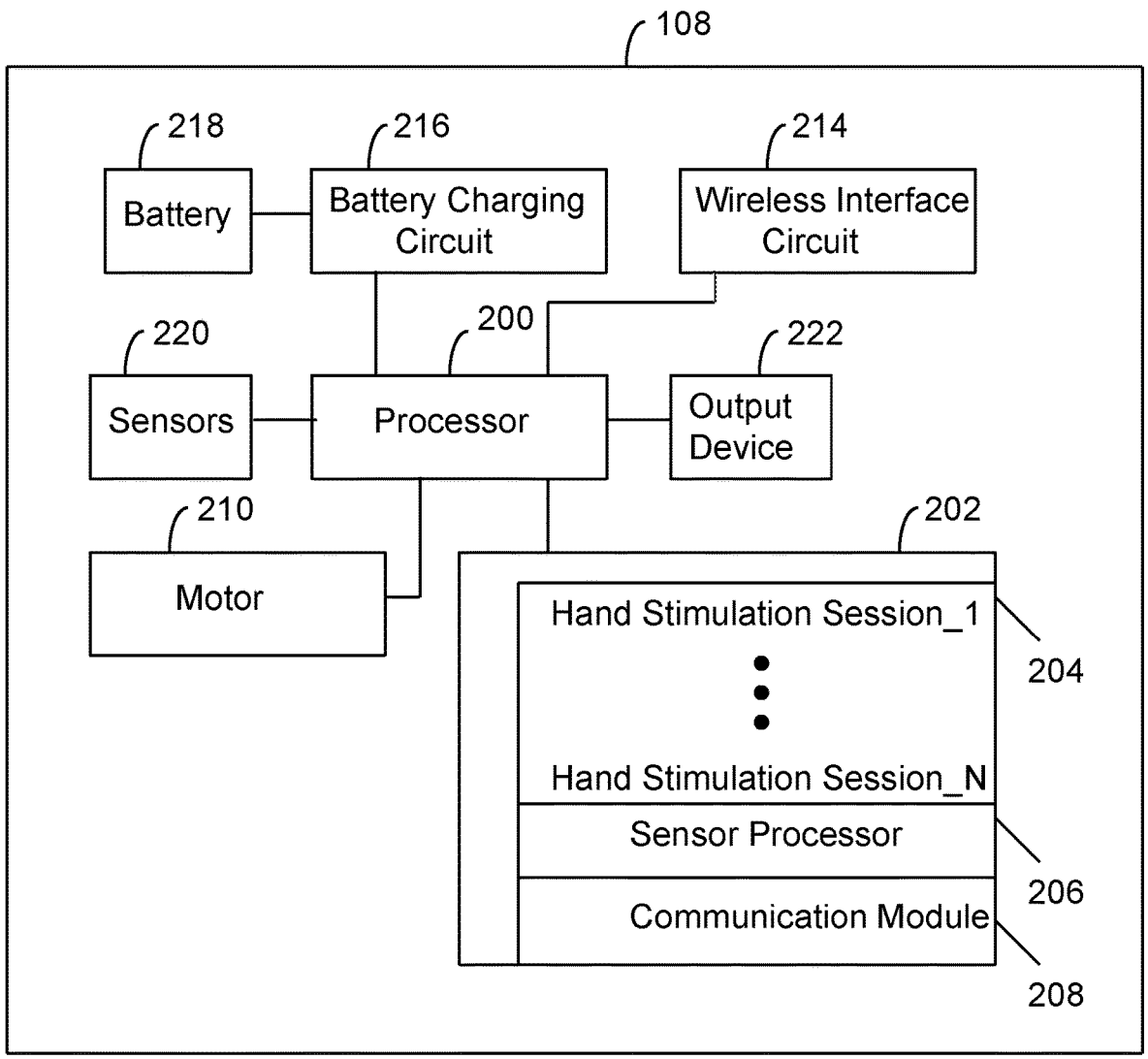
FIG. 2 illustrates electronic components associated with a hand stimulation device configured in accordance with an embodiment of the invention.

FIG. 2 illustrates an HSD 108 configured in accordance with an embodiment of the invention. The HSD 108 includes a processor 200 in communication with a memory 202. The memory 202 stores a set of hand stimulation sessions 204 (e.g., hand stimulation sessions 1 through N). Each hand stimulation session is executed by the processor 200, which coordinates motor 210 to apply vibration intensity values to the HSD 108. Each hand stimulation session is configured to guide a user into a meditative state, maintain the user in the meditative state and then guide the user out of the meditative state. Each session provides gentle, subtle rhythms and cues designed to guide and aid meditation.

The memory 202 also stores a sensor processor 206 to collect and process signals from sensors 220. By way of example, the sensors 220 may include an electrocardiogram (ECG) sensor, a moisture sensor, a temperature sensor and the like. Such signals may be evaluated to access parameters associated with a meditative state. The sensors 220 may be in the form of electrodes, as discussed below.

The memory 202 also stores a communication module 208. The communication module 208 coordinates communications between the client device 102 and/or server 104. The communication module 208 accesses the wireless interface circuit 214 to coordinate such communications. For example, the wireless interface circuit 214 receives hand stimulation sessions from the network 106, which originate at HSD session database 142 of server 104. The wireless interface circuit 214 also transmits hand stimulation session utilization data, which may be conveyed to the HSD application 122 and/or the HSD session database 142.

The HSD 108 may also include a battery charging circuit 216 and an associated battery 218. The battery charging circuit 216 may be a physical connector, such as a USB port, or an inductive connection. The HSD 108 may also include an output device 222. The output device 222 may be a display or a more basic form of output, such as a sequence of light emitting diodes (LEDs).

Figure 3:
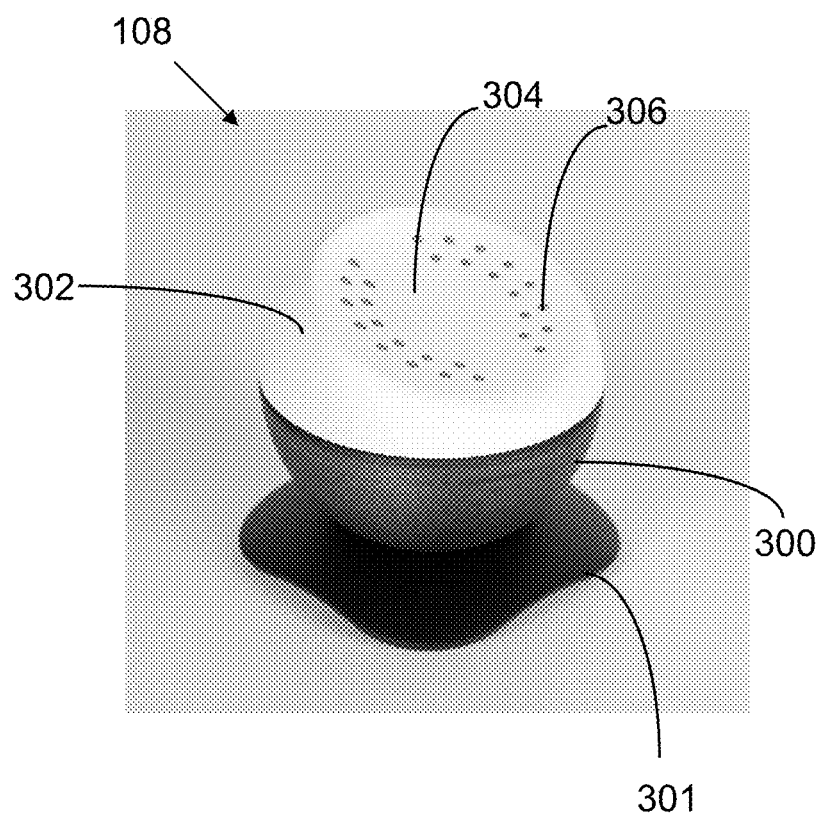
FIG. 3 is a perspective view of a housing for a hand stimulation device configured in accordance with an embodiment of the invention.

FIG. 3 is a perspective view of an HSD 108 configured in accordance with an embodiment of the invention. The HSD 108 has a bottom sphere 300. The bottom sphere is shaped like a ball, such as a round ball or an oblong ball. The shape of the sphere is selected to facilitate comfortable engagement with a hand of a user. The bottom sphere 300 may have a smooth surface, a dimpled surface or a textured surface. In one embodiment, the bottom sphere 300 is formed of wood (e.g., wood with stain and a light varnish finish). The bottom sphere 300 has a bottom surface that is flat so that the bottom surface may rest on a base 301. The base 301 may include a power charging circuit for engagement with battery charging circuit 216. In one embodiment, the flat surface has a diameter of approximately 40 mm.

The HSD 108 also has a top sphere 302, which is connected to the bottom sphere 300. The point of connection defines a central plane. The top sphere 302 and bottom sphere 300 define an interior volume in which components of FIG. 2 may be housed. In one embodiment, the HSD 108 has a diameter of between 80 and 110 mm, preferably approximately 95 mm.

The top sphere 302 includes a concave surface 304 at an angle (e.g., between 30 and 60 degrees, preferably around 45 degrees) to the central plane. The concave surface 304 hosts electrodes 306. The electrodes 306 may be formed of stainless steel and protrude from the concave surface 304 by approximately 0.5 mm to 3 mm. As shown, the electrodes 306 are arrange in two concentric semi-circles on the left and right half of the concave surface 304. This facilitates engagement of the right and left thumbs of a user. The top sphere 302 may have a smooth surface, a dimpled surface or a textured surface. In one embodiment, the top sphere 302 is formed of plastic with a matte finish.

Figure 4:
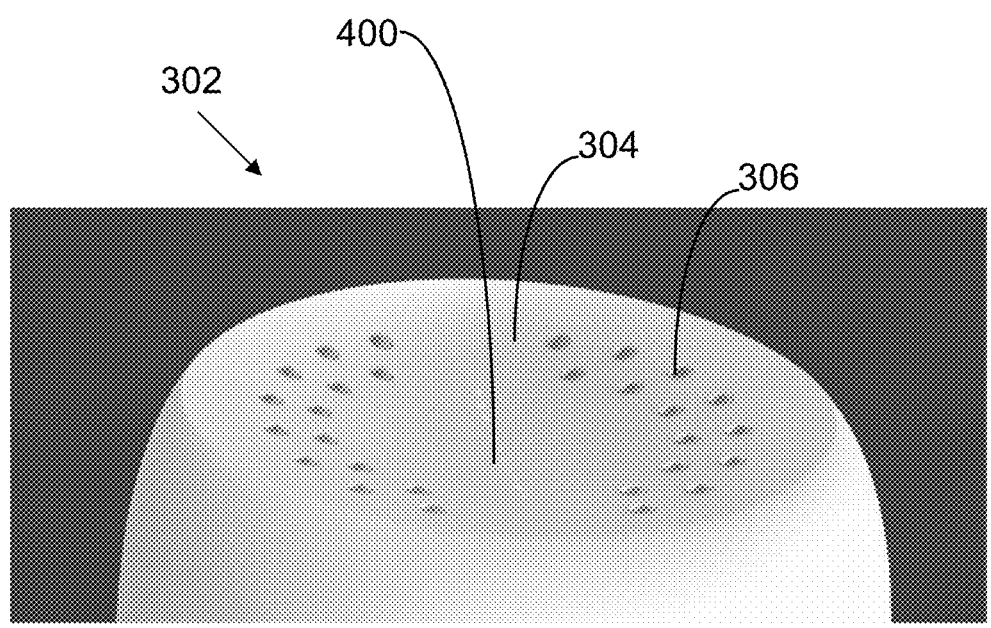
FIG. 4 is a front view of a top sphere of a hand stimulation device configured in accordance with an embodiment of the invention.

FIG. 4 is a more detailed view of the top sphere 302. The figure illustrates concave surface 304 and electrodes 306. The figure also illustrates a set of LEDs 400 in the center of the concave surface 304. The LEDs 400 are operative as an output device 222 to convey such information as, device on, session progress, and the like. In one embodiment, there are 9 white LEDs and 1 RGB LED. The LEDs may be used to communicate information, such as session progress, biofeedback results and diagnostic information, such as charging, low battery, Bluetooth® pairing and the like.

Figure 5:
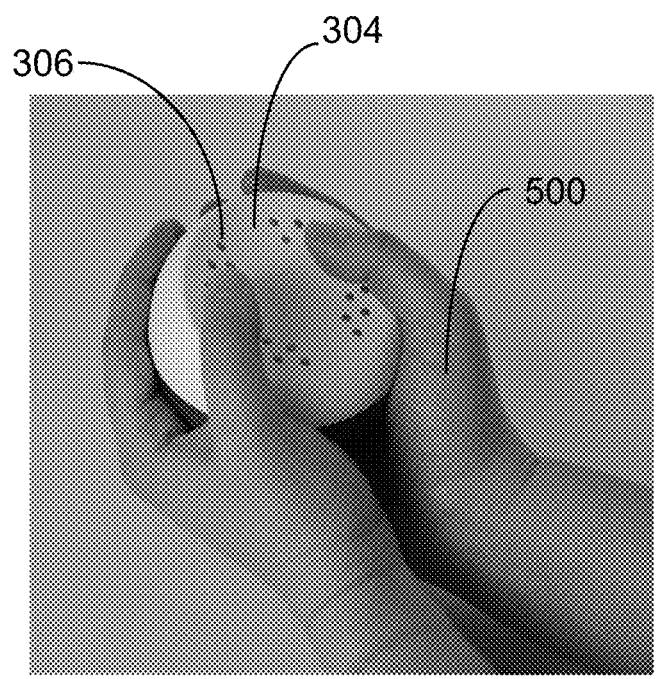
FIG. 5 illustrates a user engaging a hand stimulation device configured in accordance with an embodiment of the invention.

FIG. 5 illustrates a hand 500 of a user engaging the HSD. More particularly, the figure illustrates the thumbs of a user engaging electrodes 306 of the concave surface 304. In one embodiment, the electrodes 306 are stainless steel with a matte finish. The electrodes may be domed and protrude 1 mm or less from the concave surface 304. The electrodes 306 may be circular, rectangular or any other polygonal shape. The electrodes 306 are positioned to accommodate people with different hand and finger sizes. Typically, a user's thumbs rest on two or more electrodes 306 in natural reach. Other fingers may be used to engage the electrodes 306. The HSD may be configured without electrodes. In such a case, the vibration intensity values applied to the motor vibrate the entire HSD, but the user does not have the additional tactile sensation provided by the electrodes.

One or more of the electrodes 306 may be substituted with a sensor of the type earlier described. In one embodiment, the sensors measure electrocardiogram (ECG) signals from a user via contact with hands. The ECG data is used to analyze heart health, heart rate, heart rate variability, respiration rate and nervous system activity. In particular, the P, Q, R, S and T waves of ECG activity are analyzed. These metrics are used to determine personal heart rate variability baselines, stress and calm thresholds for stressed and calm states, and indicators related to additional health goals, such as fitness and risk of over-training, risk of fatigue, smoking cessation, weight loss, stress management, anxiety, mental health and the like.

The ECG data may be processed by the sensor processor 206 of HSD 108, the HSD application 122 on client 102 and/or the sensor signal processor 144 on server 104. The sensor data may be used to alter vibration intensity values or information conveyed by the output device 222. The sensor signal processor 144 may evaluate sensor signals to derive new HSD sessions, which are loaded into HSD session DB 142. Such sessions may also be downloaded to the HSD application 122, which may convey it to the HSD 108 via a Bluetooth® connection. The sensor signal processor 144 may also generate data for consumption by the analytics module 146. The HSD application 122 may query the analytics module 146 for various HSD analytical activity. For example, a user may obtain data about a single session, multiple sessions over time and suggested sessions. In one embodiment, the HSD application 122 is used to play an audio guided meditation track while the HSD 108 is used. The audio track may be obtained from the HSD session database 142.

Attention now turns to different hand stimulation sessions that may be utilized in accordance with embodiments of the invention. As previously discussed, a hand stimulation session includes a sequence of cycles. Each cycle is a sequence of vibration intensity values applied to electrodes. The vibration intensity values may be characterized as a percentage of the maximum vibration intensity of motor 210.

Hand stimulation sessions 204 may be obtained from HSD session database 142. For example, in one embodiment, HSD application 122 of client 102 is used to communicate with server 104 via network 106. More particularly, the HSD application 122 views and selects HSD sessions from the HSD session database 142. The HSD application 122, may then convey an HSD session to the HSD utilizing the wireless interface circuit 214 of the HSD 108. In one embodiment, the HSD application 122 allows a session to be altered for user preference, instructor control and/or biofeedback.

One type of HSD session is referred to as a breathing cycle session. The breathing cycle session mimics a human breathing rhythm at a rate and pattern that is optimal for the body's homeostatic processes, efficiency of the heart and autonomic nervous system activities, and recovery. For most people, this optimal breathing rate is between 4.5 and 7 breaths per minute (BPM), with the average at 6 BPM. Forty percent of a respiration cycle is spent in inhale and 60% in exhale. The breathing cycle session is designed accordingly, so that the vibration is a breathing guide that aids the user to achieve optimal recovery during a session. The user inhales as the vibration intensity ramps up and exhales as it ramps down.

Figure 6:
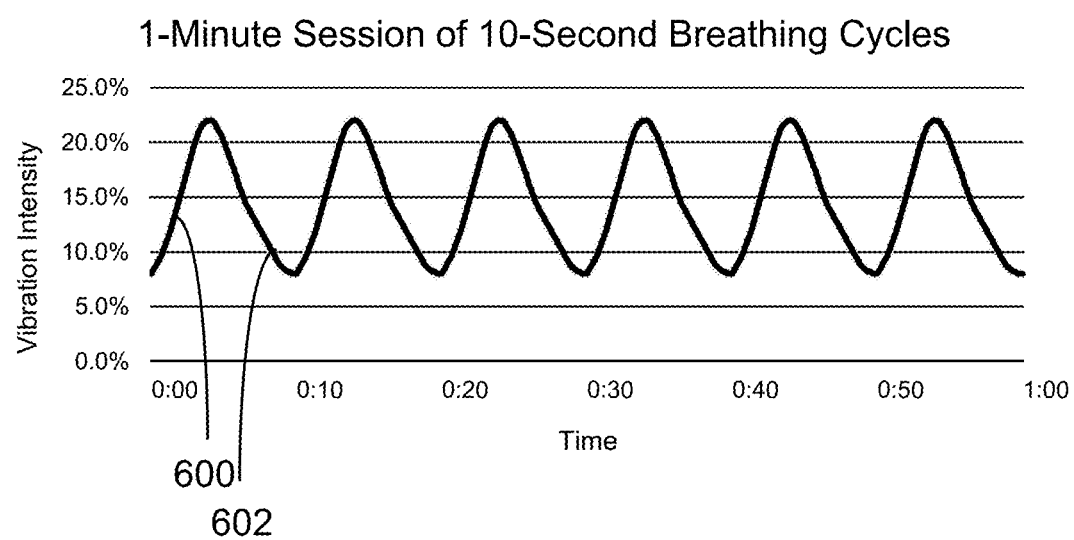
FIG. 6 illustrates a breathing session executed by the hand stimulation device in accordance with an embodiment of the invention.

A one minute long session made up of 10-second Breathing Cycles (for the average optimal breathing rate of 6 BPM) is shown in FIG. 6. Each cycle includes rising vibration intensity values 600 followed by falling vibration intensity values 602 for a total cycle duration of approximately 10 seconds. In general, each cycle should be between six and twelve seconds.

Figure 7:
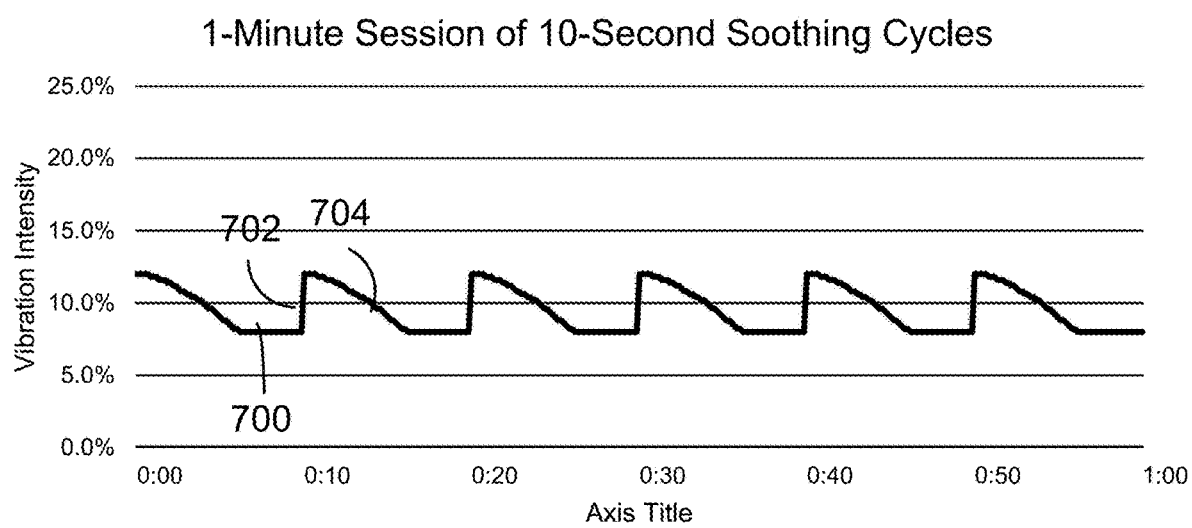
FIG. 7 illustrates a soothing session executed by the hand stimulation device in accordance with an embodiment of the invention.

FIG. 7 illustrates a soothing session with a soothing rhythm to relax and release tension as vibration intensity values fall. As shown in FIG. 7, each cycle includes consistent nominal vibration intensity values 700 followed by at least one rising vibration intensity value 702 followed by falling vibration intensity values 704 for a total cycle duration of approximately 10 seconds. In general, each cycle should be between six and twelve seconds.

Figure 8:
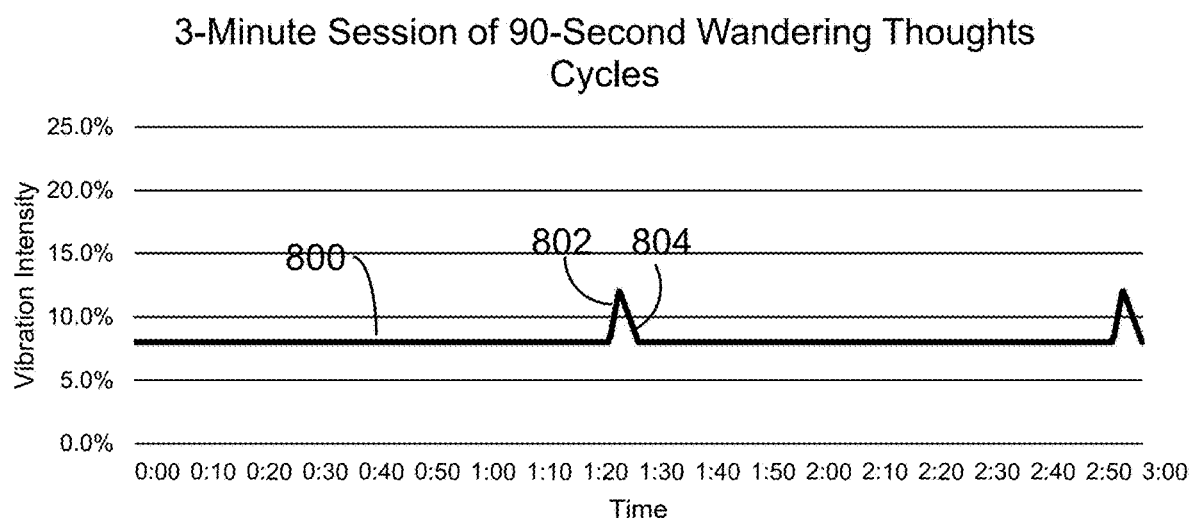
FIG. 8 illustrates a wandering thoughts session executed by the hand stimulation device in accordance with an embodiment of the invention.

FIG. 8 illustrates a wandering thoughts session. This session involves subtle constant input and periodic pulses at intervals that would commonly be used by meditation instructors to help meditators become aware if their thoughts have wandered from the meditation's point of focus. That is, the periodic pulses nudge meditators to bring their thoughts and attention back into meditation. As shown in FIG. 8, each cycle includes consistent nominal vibration intensity values 800 followed by at least one rising vibration intensity value 802 followed by falling vibration intensity values 804. The consistent nominal vibration intensity values 800 are at least three-quarters of each cycle. In the example of FIG. 8, the consistent nominal vibration intensity values 800 are over a minute and the rising vibration intensity value 802 followed by falling vibration intensity values 804 are approximately ten seconds or less.

Figure 9:
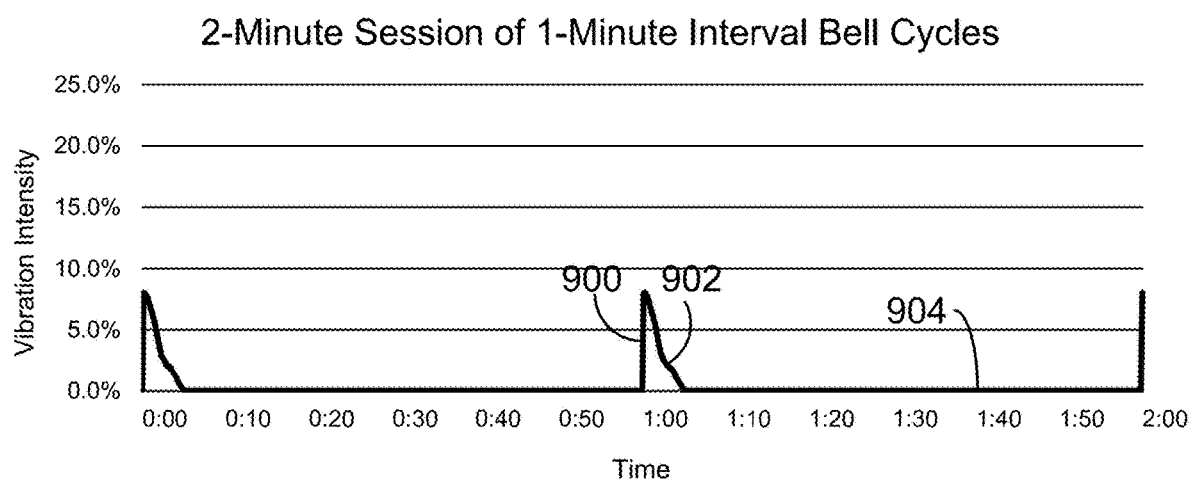
FIG. 9 illustrates an interval bell session executed by the hand stimulation device in accordance with an embodiment of the invention.

FIG. 9 illustrates an interval bells session. Each cycle has at least one rising vibration intensity value 900 followed by falling vibration intensity values 902, followed by absent vibration intensity values 904. The at least one rising vibration intensity value 900 followed by falling vibration intensity values 902 are a quarter or less of each cycle. In the example of FIG. 9 they are approximately five seconds of a sixty second cycle or one-twelfth of a cycle.

Figure 10:
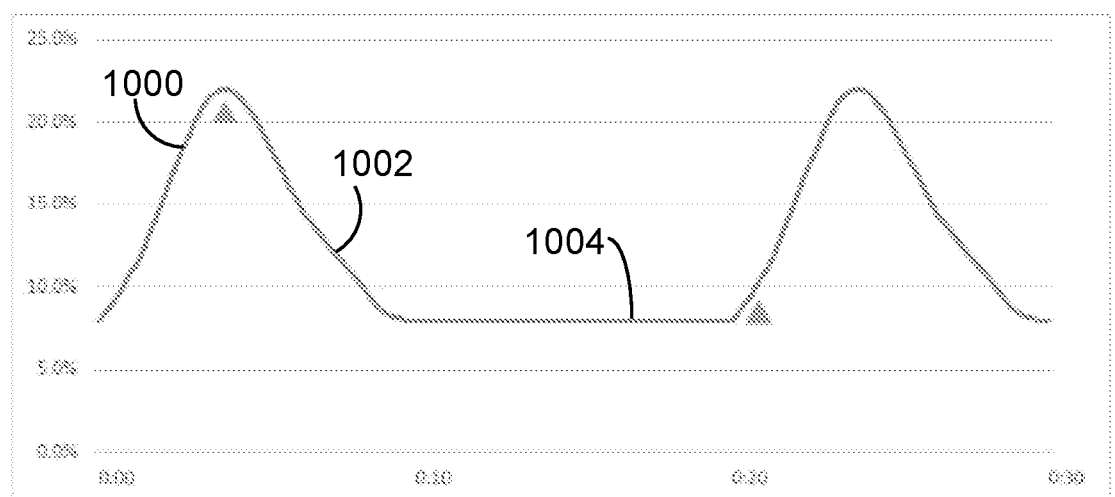
FIG. 10 illustrates an instructor session executed by the hand stimulation device in accordance with an embodiment of the invention.

FIG. 10 illustrates an instructor session. This session may be used with a live or recorded instructor to facilitate rhythmic counting, controlled breathing exercises and physical awareness exercises. Each cycle includes rising vibration intensity values 1000 followed by falling vibration intensity values 1002 followed by consistent nominal vibration 1004 intensity values. The rising vibration intensity values 1000 followed by the falling vibration intensity values 1002 have a combined duration approximately equal to duration of the consistent nominal vibration intensity values 1004.

Figure 11:
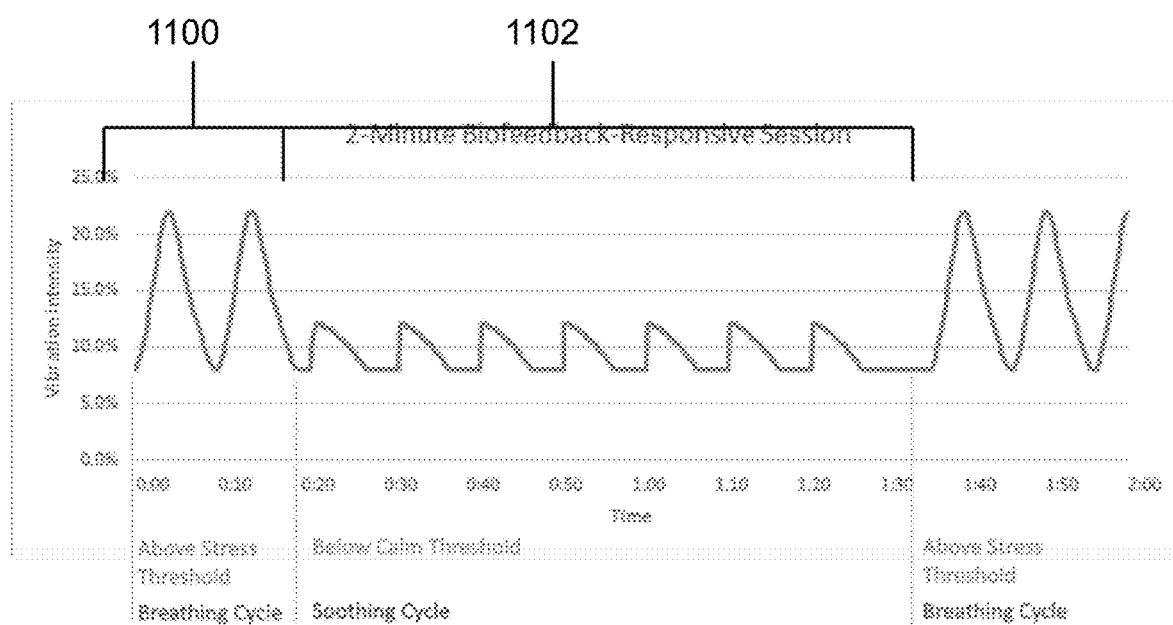
FIG. 11 illustrates a biofeedback session executed by the hand stimulation device in accordance with an embodiment of the invention.

FIG. 11 illustrates a biofeedback session. A user's biofeedback is used to dynamically alter the sequence of cycles for a session. Biometric thresholds are set that represent stress and calm states, and different cycles are chosen for each state. Any cycle can be used for any given biometric state. The choice of cycle for each state is made either by pre-set defaults, analyzing previous sessions and other users' data to select cycle sequences that have been most effective for the specific user (or for users like her), user choice or instructor choice. The session of FIG. 11 uses the breathing cycle when a user is above a biometric stress threshold, in order to help calm down the user. Upon achieving a calm biometric threshold, the vibration fades into the soothing cycle. If the user returns to the stressed state, the breathing cycle starts again. That is, FIG. 11 illustrates a breathing session segment, followed by a soothing session segment. In the breathing session segment each cycle includes rising vibration intensity values followed by falling vibration intensity values, as shown in FIG. 6. In the soothing session segment each cycle includes consistent nominal vibration intensity values followed by at least one rising vibration intensity value followed by falling vibration intensity values, as shown in FIG. 7. The biofeedback session includes a sequence of breathing session segments 1100 followed by a sequence of soothing session segments 1102. The sequence of soothing session segments 1102 are at least twice as long as the sequence of breathing session segments 1100.

Figure 12:
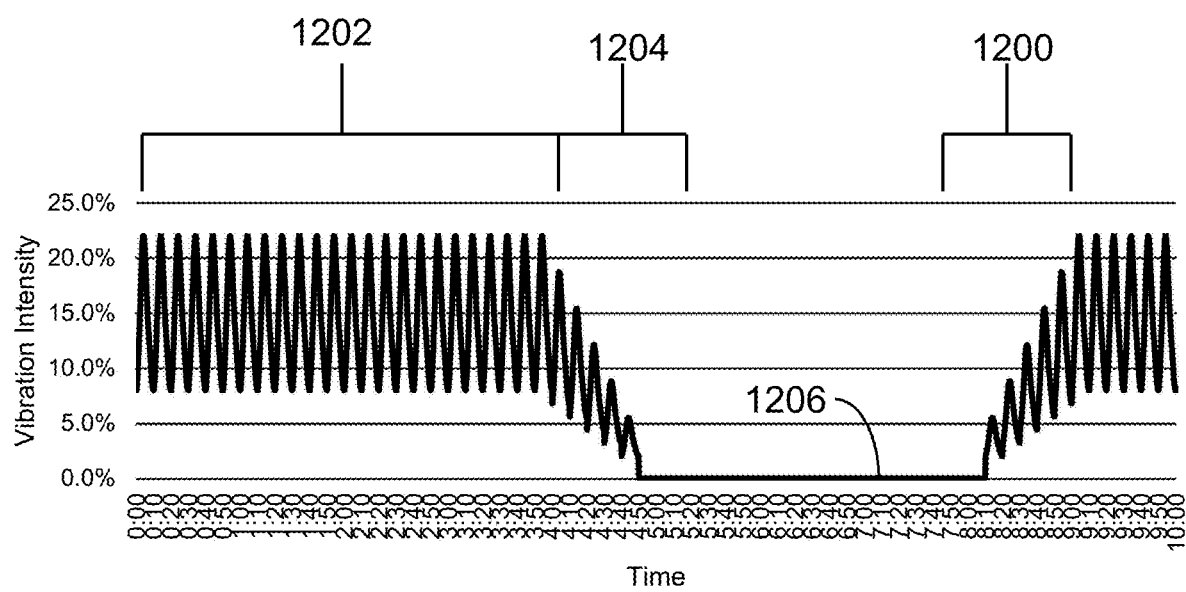
FIG. 12 illustrates a fade session executed by the hand stimulation device in accordance with an embodiment of the invention.

FIG. 12 illustrates a fade session. For any of the sessions described here, an optional fade is applied. This means that approximately 40% through a timed meditation, or after a set number of minutes, the vibration cycles slowly fade out, as the user is deep in her meditation flow. The cycles slowly fades back in at approximately 85% through the meditation or after a set number of minutes. This allows the user to gently become aware of her physical surroundings and sensations as she ends a meditation session—a tangible version of instructor guidance towards the end of a session to become aware of physical feelings, sounds, and physical surroundings before opening one's eyes and completing a meditation.

FIG. 12 illustrates a ramp up session segment 1200 with a first sequence of cycles where each cycle in the first sequence of cycles has rising vibration intensity values followed by falling vibration intensity values that are greater than rising vibration intensity values and falling vibration intensity values of a previous cycle. A steady state session segment 1202 has substantially identical rising vibration intensity values followed by falling vibration intensity values. A ramp down session segment 1204 has a second sequence of cycles where each cycle in the second sequence of cycles has rising vibration intensity values followed by falling vibration intensity values that are greater than rising vibration intensity values and falling vibration intensity values of a subsequent cycle. A quiescent session segment 1206 omits vibration intensity values. The ramp up session segment 1200 is less than a quarter of the fade session duration, the steady state session segment 1202 is at least one half of the fade session duration, the ramp down session segment 1204 is less than a quarter of the fade session segment, and the quiescent session segment 1206 is less than a quarter of the fade session duration.

An embodiment of the present invention relates to a computer storage product with a computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs, DVDs and holographic devices; magneto-optical media; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, or other object-oriented programming language and development tools. Another embodiment of the invention may be implemented in hardwired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. An apparatus, comprising:
a bottom sphere;
a top sphere connected to the bottom sphere to define an interior volume with a central plane, wherein the top sphere includes a concave surface at an angle to the central plane;
a motor positioned within the interior volume;
a processor positioned within the interior volume and connected to the motor; and
a memory positioned within the interior volume and connected to the processor, the memory storing instructions which are configured to be executed by the processor, wherein the instructions include hand stimulation sessions, each hand stimulation session comprising a sequence of cycles, wherein each cycle is a sequence of vibration intensity values applied to the motor and wherein the hand stimulation sessions include a biofeedback session comprising:
a breathing session segment wherein each cycle includes rising vibration intensity values followed by falling vibration intensity values for a total cycle duration of between six and twelve seconds;
a soothing session segment wherein each cycle includes consistent nominal vibration intensity values followed by at least one rising vibration intensity value followed by falling vibration intensity values for a total cycle duration of between six and twelve seconds;
wherein the biofeedback session includes a sequence of breathing session segments followed by a sequence of soothing session segments, wherein the sequence of soothing session segments are at least twice as long as the sequence of breathing session segments.

2. The apparatus of claim 1 wherein the bottom sphere is formed of wood.

3. The apparatus of claim 1 wherein the top sphere is formed of plastic.

4. The apparatus of claim 1 wherein the concave surface hosts electrodes.

5. The apparatus of claim 1 further comprising sensors positioned on the concave surface.

6. The apparatus of claim 1 further comprising a wireless communication circuit positioned within the interior volume and connected to the processor.

7. The apparatus of claim 6 wherein the wireless communication circuit is configured to receive the hand stimulation sessions.

8. The apparatus of claim 6 wherein the wireless communication circuit is configured to transmit hand stimulation session utilization data.

9. The apparatus of claim 6 in combination with a mobile device configured for executing an application that coordinates operation of the apparatus.

10. The apparatus of claim 9 in combination with a server in network communication with the mobile device.

11. An apparatus, comprising:
a bottom sphere;
a top sphere connected to the bottom sphere to define an interior volume with a central plane, wherein the top sphere includes a concave surface at an angle to the central plane;
a motor positioned within the interior volume;
a processor positioned within the interior volume and connected to the motor; and
a memory positioned within the interior volume and connected to the processor, the memory storing instructions configured to be executed by the processor, wherein the instructions include hand stimulation sessions, each hand stimulation session comprising a sequence of cycles, wherein each cycle is a sequence of vibration intensity values applied to the motor and wherein the hand stimulation sessions include a fade session comprising;
a ramp up session segment with a first sequence of cycles wherein each cycle in the first sequence of cycles has rising vibration intensity values followed by falling vibration intensity values that are greater than rising vibration intensity values and falling vibration intensity values of a previous cycle;
a steady state session segment wherein each cycle has substantially identical rising vibration intensity values followed by falling vibration intensity values;

a ramp down session segment with a second sequence of cycles wherein each cycle in the second sequence of cycles has rising vibration intensity values followed by falling vibration intensity values that are greater than rising vibration intensity values and falling vibration intensity values of a subsequent cycle; and a quiescent session segment without vibration intensity values;

wherein the ramp up session segment is less than a quarter of the fade session duration, the steady state session segment is at least one half of the fade session duration, the ramp down session segment is less than a quarter of the fade session segment, and the quiescent session segment is less than a quarter of the fade session duration.

12. The apparatus of claim 11 wherein the bottom sphere is formed of wood.

13. The apparatus of claim 11 wherein the top sphere is formed of plastic.

14. The apparatus of claim 11 wherein the concave surface hosts electrodes.

15. The apparatus of claim 11 further comprising sensors positioned on the concave surface.

16. The apparatus of claim 11 further comprising a wireless communication circuit positioned within the interior volume and connected to the processor.

17. The apparatus of claim 16 wherein the wireless communication circuit is configured to receive the hand stimulation sessions.

18. The apparatus of claim 16 wherein the wireless communication circuit is configured to transmit hand stimulation session utilization data.

19. The apparatus of claim 16 in combination with a mobile device is configured for executing an application that coordinates operation of the apparatus.

20. The apparatus of claim 19 in combination with a server in network communication with the mobile device.

* * * * *